United States Patent [19]

Kümmerle et al.

[11] 4,128,578

[45] Dec. 5, 1978

[54] PROCESS FOR THE MANUFACTURE OF 3-HYDROXYBUTYRIC ACID ARYLAMIDES WITH TRIALKYL PHOSPHATE AND SUBSTITUTED PHOSPHINE PROMOTOR

[75] Inventors: Kurt Kümmerle, Kelkheim; Hartmut Heise, Bad Soden am Taunus; Ernst Hille, Kelkheim, all of Fed. Rep. of Germany

[73] Assignee: Hoechst Aktiengesellschaft, Frankfurt am Main, Fed. Rep. of Germany

[21] Appl. No.: 775,461

[22] Filed: Mar. 8, 1977

[30] Foreign Application Priority Data

Mar. 10, 1976 [DE] Fed. Rep. of Germany ....... 2609835

[51] Int. Cl.$^2$ .................. C07B 1/00; C07C 102/00
[52] U.S. Cl. .................. 260/562 R; 260/690; 252/430; 252/431 P
[58] Field of Search .................. 260/562 R, 690; 252/430, 431 P

[56] References Cited

U.S. PATENT DOCUMENTS

| | | | |
|---|---|---|---|
| 2,830,087 | 4/1958 | Ehrhart et al. | 260/562 A |
| 3,051,618 | 8/1962 | Ehrhart et al. | 260/562 R |
| 3,130,237 | 4/1964 | Wald | 260/690 X |
| 3,642,658 | 2/1972 | Allum et al. | 252/431 P |
| 3,737,459 | 6/1973 | Fenton | 252/431 P |
| 3,819,734 | 6/1974 | Kothari et al. | 252/431 P |
| 3,992,323 | 11/1976 | Yoo et al. | 252/430 |
| 4,005,143 | 1/1977 | Bohm et al. | 252/430 |

OTHER PUBLICATIONS

Adkins et al., J. Am. Chem. Soc. 70 (1948), pp. 695–698.

*Primary Examiner*—Allen B. Curtis
*Attorney, Agent, or Firm*—Curtis, Morris & Safford

[57] ABSTRACT

The liquid-phase catalytic hydrogenation of N-acetoacetyl arylamides to yield 3-hydroxybutyric acid arylamides proceeds much faster when amines, phosphines or trialkylphosphates are added. Thus, even with lower hydrogen pressures and at lower temperatures with a lower catalyst concentration, shorter reaction times are sufficient.

17 Claims, No Drawings

PROCESS FOR THE MANUFACTURE OF 3-HYDROXYBUTYRIC ACID ARYLAMIDES WITH TRIALKYL PHOSPHATE AND SUBSTITUTED PHOSPHINE PROMOTOR

It is known that 3-hydroxybutyric acid arylamides may be manufactured by catalytic hydrogenation of N-acetoacetyl arylamides (U.S. Pat. No. 2,830,087).

It has now been found that the catalytic hydrogenation of N-acetoacetyl arylamides in the liquid phase may be carried out in an especially advantageous manner with the addition of amines, phosphines or trialkyl phosphates as promotors.

The promotors in accordance with this invention cause the reaction to proceed much more rapidly than hitherto known, so that the hydrogenation is complete after a short period even under low reaction pressure and at low catalyst concentration. Therefore, the use of expensive high pressure reactors is no longer required in order to maintain economic reaction times, since for this invention, reactors designed for lower pressures suffice, and the operations may optionally be carried out at lower reaction temperatures.

The hydrogenation may be carried out under pressures of up to 200 atm/gage, preferably from about 40 to 50 atm/gage, and at temperatures of up to 250°, preferably from about 130° to 150° C. The catalyst concentration is up to 7.5%, generally about 2.5%, relative to the weight of the acetoacetyl arylamide.

The hydrogenation is carried out in the liquid phase, the reaction medium containing preferably an organic solvent. Water-miscible solvents, especially lower alkanols, are preferred.

Suitable N-acetoacetyl arylamides are above all those anilides and their derivatives substituted in the benzene nucleus by lower alkyl and/or lower alkoxy groups.

The promotors used in accordance with this invention are preferably liquid and miscible in any ratio with the reaction medium. The promotors may also be solid; however, they must be soluble in the reaction medium. In this latter case, the promotor is advantageously more readily soluble in the reaction medium than the reaction product, since the promotor may then be easily eliminated by washing.

Preferred promotors are amines or phosphines substituted by alkyl radicals having up to 10, preferably up to 6, and especially up to 4 carbon atoms, phenyl radicals optionally substituted by lower alkyl or lower alkoxy groups, cycloalkyl radicals having from 4 to 8 carbon atoms, or aralkyl radicals derived from lower alkyl and phenyl radicals which may be substituted as indicated above. As amines, there may furthermore be used mono- or binuclear saturated or unsaturated heterocyclic amines each having 5- or 6-membered rings, for example piperidine, morpholine, pyridine or quinoline. Preferred trialkyl phosphates are those the alkyl radicals of which contain up to 10, preferably up to 6, and especially up to 4 carbon atoms.

The amount of promotors used, relative to the weight of N-acetoacetyl arylamide, is up to about 10%, preferably up to about 5%. Generally, concentrations of about 2.5% are sufficient. By "lower" in connection with alkyl and alkoxy groups, there is to be understood that these radicals have up to 4 carbon atoms.

The following examples illustrate the invention. All percentages are by weight unless otherwise stated.

EXAMPLE 1

Acetoacetic acid-p-phenetidide was hydrogenated in isopropanol under a hydrogen pressure of 135 atm/gage and at a temperature of 135° C. in the presence of a commercial nickel carrier catalyst (nickel supported by a carrier having a large surface) to yield 3-hydroxybutyric acid-p-phenetitide:

Amounts used:
  200 g acetoacetic acid-p-phenetidide (100%)
  935 g isopropanol
  5 g nickel carrier catalyst (= 2.5% of the amount of product to be hydrogenated)
  30 Nl hydrogen (including amount for flushing; Nl = normal liter, that is, under "normal" pressure (760 torr) and a temperature of 0° C.)
  Yield: 95% of the theoretical yield.
  Hydrogenation time: 60 minutes.

After hydrogenation, the reactor was depressurized, flushed with nitrogen, and the contents of the autoclave were pressed into a receiver via a pressure filter heated at 75° C., in order to separate the catalyst. The reaction mixture was concentrated with agitation by partial evaporation of the isopropanol, the remaining suspension was cooled to about 0° C. with further agitation, and the solid final product was isolated by filtration. Drying was carried out at a partial vacuum of about 20 mm Hg and a temperature of 60° C.

When the hydrogenation is carried out under a hydrogen pressure of about 45 atm/gage, while maintaining all other reaction conditions, the hydrogenation time is 120 minutes, the yield being the same.

When 5 g of promotor (= 2.5% of the amount of product to be hydrogenated) are added, the hydrogenation times are reduced, as results from the following Table 1:

TABLE 1

| Promotor | Pressure (atm/gage) | Reaction time (Minutes) |
|---|---|---|
| none | about 135 | about 60 |
| none | " 45 | " 120 |
| butylamine | " 45 | " 60 |
| dipropylamine | " 45 | " 60 |
| triethylamine | " 45 | " 60 |
| cyclohexylamine | " 45 | " 65 |
| β-phenylethylamine | " 45 | " 75 |
| aniline | " 45 | " 75 |
| triethyl phosphate | " 45 | " 40 |

EXAMPLE 2

Amounts, reaction conditions and work-up were as described for the test series of Example 1. However, the catalyst was replaced: instead of 5 g of a nickel carrier catalyst, 5 g of an aged palladium carrier catalyst was used. The yield is again 95% of the theoretical yield. The reaction times are listed in Table 2:

TABLE 2

| Promotor | Pressure (atm/gage) | Reaction time (Minutes) |
|---|---|---|
| none | about 135 | about 200 |
| none | " 45 | " 380 |
| triethylamine | " 45 | " 190 |

EXAMPLE 3

In the test series of this Example, various catalysts, each with and without promotor substance, were used.

The hydrogen pressure was about 45 atm/gage; amounts, reaction conditions, work-up and yields were the same as in the test series of Example 2. The following reaction times resulted:

TABLE 3

| Catalyst | Promotor | Reaction time (Minutes) | |
|---|---|---|---|
| Platinum (carrier catalyst) | — | about | 60 |
| " | triethylamine | " | 30 |
| ruthenium (carrier catalyst) | — | " | 25 |
| " | triethylamine | " | 10 |
| Raney-nickel (skeleton catalyst) | — | " | 55 |
| " | triethylamine | " | 30 |
| " | triethyl phosphate | " | 20 |

EXAMPLE 4

Acetoacetic acid anilide in isopropanol was catalytically hydrogenated under a hydrogen pressure of about 45 atm/gage and at a temperature of 135° C. to yield 3-hydroxybutyric acid anilide. Hydrogenation operations, work-up of the final product and its drying were as described in Example 1:

Amounts:
180 g acetoacetic acid anilide (100%)
900 g isopropanol
5 g catalyst (see Table 4)
5 g promotor (see Table 4)
30 Nl hydrogen (including hydrogen for flushing)
Yield: 94% of the theoretical yield.

The reaction times are listed in Table 4.

TABLE 4

| Catalyst | Promotor | Reaction time (Minutes) | |
|---|---|---|---|
| nickel (carrier catalyst) | — | about | 120 |
| " | propylamine | " | 60 |
| " | butylamine | " | 60 |
| " | triethylamine | " | 60 |
| " | triethyl phosphate | " | 40 |
| platinum (carrier catalyst) | — | " | 60 |
| " | triethylamine | " | 30 |
| Raney-nickel (skeleton catalyst) | — | " | 50 |
| " | triethylamine | " | 25 |

We claim:

1. In a process for the liquid-phase catalytic hydrogenation of N-acetoacetyl arylamides to yield 3-hydroxybutyric acid arylamides at elevated temperatures the improvement comprising adding to the reaction mixture an effective amount of a promoter selected from phosphines, trialkyl phosphates and mixtures thereof to promote said catalytic hydrogenation.

2. A process as claimed in claim 1, wherein the trialkyl phosphate contains three equal or different alkyls of 1 to 10 carbon atoms.

3. A process as claimed in claim 1, wherein up to 10%, referred to the weight of the N-acetoacetyl arylamide, of phosphine or trialkyl phosphate are added.

4. A process as claimed in claim 3, wherein the amount is up to 5%.

5. A process as claimed in claim 1, wherein the hydrogenation is effected at a pressure of up to 200 atm/gage.

6. A process as claimed in claim 5, wherein the pressure is 40 to 50 atm/gage.

7. A process as claimed in claim 1, wherein the temperature is up to 200° C.

8. A process as claimed in claim 7, wherein the temperature is 130° to 150° C.

9. A process as claimed in claim 1, wherein an effective amount of up to 7.5%, referred to the weight of acetoacetyl arylamide, of hydrogenation catalyst is present.

10. A process as claimed in claim 9, wherein the amount is about 2.5%.

11. A process as claimed in claim 1, wherein the hydrogenation reaction medium contains an organic solvent.

12. A process as claimed in claim 11, wherein the solvent is water-miscible.

13. A process as claimed in claim 11, wherein the solvent is a lower alkanol.

14. A process as claimed in claim 1, wherein the arylamide is the anilide which is unsubstituted or substituted in the benzene nucleus by lower alkyl and/or lower alkoxy.

15. A process as claimed in claim 1, wherein the arylamide is the anilide or the p-phenetidide.

16. In a process for the liquid phase catalytic hydrogenation of N-acetoacetyl arylamides at elevated temperatures to yield 3-hydroxybutyric acid arylamides, the improvement which comprises incorporating in the reaction mixture an effective amount of a promoter which is a phosphine, said phosphines selected from the group of phosphines substituted by 1 to 3 substituents selected from the group consisting of alkyl of 1 to 10 carbon atoms, cycloalkyl of 4 to 8 carbon atoms, phenyl, phenyl substituted by lower alkyl or lower alkoxy and lower alkyl substituted by phenyl which phenyl is unsubstituted or substituted by lower alkyl or lower alkoxy.

17. In a process for the liquid phase catalytic hydrogenation of N-acetoacetyl arylamides at elevated temperatures to yield 3-hydroxybutyric acid arylamides, the improvement which comprises incorporating in the reaction mixture an effective amount of a promoter which is a trialkyl phosphate.

* * * * *